United States Patent [19]

Esselborn et al.

[11] Patent Number: 5,296,573

[45] Date of Patent: * Mar. 22, 1994

[54] POLYACRYLATE ESTER WITH LONG-CHAIN ALKOXYLATED HYDROCARBONOXY GROUPS AND THEIR USE IN COSMETICS AND PERSONAL GROOMING

[75] Inventors: Eberhard Esselborn; Jürgen Fock; Götz Koerner; Dietmar Schaefer, all of Essen, Fed. Rep. of Germany

[73] Assignee: Th. Goldschmidt AG, Essen, Fed. Rep. of Germany

[*] Notice: The portion of the term of this patent subsequent to Jul. 28, 2009 has been disclaimed.

[21] Appl. No.: 648,725

[22] Filed: Jan. 31, 1991

[30] Foreign Application Priority Data

Feb. 27, 1990 [DE] Fed. Rep. of Germany ....... 4006093

[51] Int. Cl.$^5$ .................... C08F 220/26; C08F 220/28
[52] U.S. Cl. ..................................... 526/320; 424/401; 514/772.6
[58] Field of Search ...................... 424/401; 514/772.6; 526/320

[56] References Cited

U.S. PATENT DOCUMENTS 4,469,611 9/1984 Snyder, Jr. et al. .
4,552,685 11/1985 Kernstock et al. .
5,133,898 7/1992 Fock et al. ........................... 252/356

FOREIGN PATENT DOCUMENTS 0011806 6/1980 European Pat. Off. .
3636429 8/1987 Fed. Rep. of Germany .

*Primary Examiner*—Gary Geist
*Attorney, Agent, or Firm*—Anderson Kill Olick & Oshinsky

[57] ABSTRACT

Polyacrylate esters with long-chain alkoxylated hydrocarbonoxy groups are disclosed which can be obtained by the transesterification of polyacrylate esters with polyoxyalkylene monools, wherein the polyacrylate esters, up to 50% of which can be replaced by the corresponding methacrylate esters, have been obtained by free radical polymerization and wherein the polyoxyalkylene monools have the average formula $$R^1O(C_nH_{2n}O-)_xH$$

wherein
  $R^1$ is an alkyl, alkenyl or alkylphenyl group,
  n has an absolute value of 2, 3 or 4 and an average value of 2.0 to 2.5 and
  x is 10 to 200.

The compounds, which can be used as emulsifiers, solubilizers and for thickening aqueous solutions which contain anionic surfactants, particularly in cosmetics and for personal grooming, are distinguished by a content of low molecular weight components, which is smaller compared to that of products obtained by copolymerization.

14 Claims, No Drawings

POLYACRYLATE ESTER WITH LONG-CHAIN ALKOXYLATED HYDROCARBONOXY GROUPS AND THEIR USE IN COSMETICS AND PERSONAL GROOMING

BACKGROUND OF THE INVENTION

The invention is directed to polyacrylate esters with long-chain alkoxylated hydrocarbonoxy groups and their use as emulsifiers, solubilizers and thickeners for aqueous, anionic surfactant-containing solutions, particularly in cosmetics and personal grooming. More particularly, the invention relates to polyacrylate esters with a reduced content of low molecular weight or oligomeric compounds, as well as with a distribution of polymers which approximates a Poisson distribution, and particularly to those polyacrylate esters, which have improved physiological properties.

Copolymers of polyoxyalkylene (meth)acrylate esters and alkyl (meth)acrylate esters are known from the art.

For example, in Japanese Published Patent Application 61/145254, organic and inorganic pigments are described, the surfaces of which are treated with a copolymer which consists of 1 to 99% by weight of polyoxyalkylene (meth)acrylate and 1 to 99% by weight of alkyl (meth)acrylate and the alkyl group of the alkyl methacrylate has 6 to 22 carbon atoms. These copolymers increase the dispersibility of pigments which have been treated with them.

From German Offenlegungsschrift 36 36 429, polymeric surfactants are known which are based on copolymers of hydrophobic and hydrophilic monomers and which contain in copolymerized form (a) as hydrophobic monomers, compounds of formula

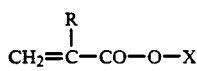

in which
R=H or CH$_3$
X=C$_4$ to C$_{20}$ alkyl or

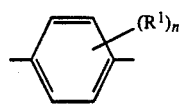

R$^1$=H, C$_1$ to C$_{20}$ alkyl or halogen

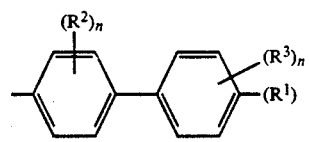

n=1 to 4
R$^2$, R$^3$=H, C$_1$ to C$_{20}$ alkyl, F, Cl, Br, and
(b) as hydrophilic monomers, compounds of the formula

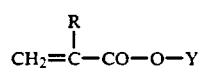

in which
R=H or CH$_3$,
Y=

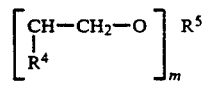

R$^4$=H, CH$_3$ or C$_2$H$_5$
R$^5$=H, C$_1$ to C$_4$ alkyl and
m=2 to 50.

In aqueous systems above the critical micelle concentrations, these polymeric surfactants form micellar structures, which, in the case of suitable formations and in particular concentration ranges, are present as liquid crystalline phases (mesophases). The copolymers described in the German Offenlegungsschrift 36 36 429 are intended to make possible a wide variation of mesophasic structures and stability parameters. These copolymers have surfactant properties and the water-soluble compounds can be used in detergent formulations to enhance laundering power. The copolymers furthermore can be used to increase the viscosity of aqueous phases, the viscosity-increasing effect being largely independent of the pH.

European published patent application 0 011 806 relates to a liquid emulsion polymer which has a ph-dependent thickening effect on aqueous preparations and contains a) 15-60% by weight of an α,β-ethylenically unsaturated monomeric carboxylic acid of the formula

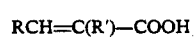

wherein
R is either a hydrogen group and R' is a hydrogen group or an alkyl group with 1 to 4 carbon atoms, or
R is a —COOX group and R' is a hydrogen group or the —CH$_2$COOX group, or
R is a methyl group and R' is a hydrogen group, and
X is a hydrogen group or an alkyl group with 1 to 4 carbon atoms b) 15-80% by weight of at least one nonionic, copolymerizable α,β-ethylenically unsaturated monomer of the formula

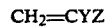

wherein
Y is a hydrogen group and Z is a —COOR, —C$_6$H$_4$-R'—, —CN—, Cl—, —OOCR"— or —CH=CH$_2$ group or
Y is a methyl group and Z a —COOR—, —C$_6$H$_4$-R'—, —CN— or —CH=CH$_2$ group or
Y and Z are chloro groups and
R is an alkyl group with 1 to 8 carbon atoms or a hydroxyalkyl group with 2 to 8 carbon atoms,
R' is a hydrogen, chloro, bromo or alkyl group with 1 to 4 carbon atoms and
R" is an alkyl group with 1 to 8 carbon atoms, and
c) 1-30% by weight of a nonionic surface active vinyl ester of the formula

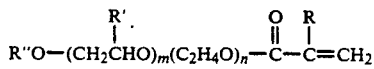

wherein
R is a hydrogen or methyl group and each R' group is an alkyl group with 1 or 2 carbon
R" is an alkyl group with 8 to 20 carbon atoms or an alkylphenyl group with 8 to 16 carbon atoms,
n on the average is a number from 6 to 100 and
m on the average is a number from 0 to 50, with the proviso that n≧m and (n+m) is equal to 6 to 100.

At a pH of less than about 5.0, the polymer is stable in the form of an aqueous colloidal dispersion. However, when the pH is adjusted to a value of 5.5 to 10.5 and higher, it becomes an effective thickener for aqueous systems.

Copolymers of a similar composition are described in U.S. Pat. Nos. 4,469,611 and 4,552,685. Gel chromatographic analysis of these copolymers of the state of the art shows a relatively broad molecular weight distribution, which can be responsible for a decreased surfactant activity. As can furthermore be demonstrated by NMR spectroscopic analysis and gel chromatographic analysis, the copolymers contain appreciable portions of low molecular weight compounds. These low molecular weight portions consist of appreciable amounts of residual monomers as well as of low molecular weight compounds. It is assumed that the cause for this may be found in the polymerization parameters of the different monomers, which differ greatly from one another.

These low molecular weight portions are, however, undesirable in various ways. They adversely affect and diminish the surface active properties of the known copolymers, since they themselves contribute nothing or only very little to these properties. The low molecular weight portions are, however, also undesirable for physiological reasons, since they lead to impairment of health, such as skin irritations, sensitizations, etc.

It is not possible to separate these interfering portions from the copolymers of the state of the art in an economic manner.

SUMMARY OF THE INVENTION

It is an object of the invention to provide improved polyacrylate esters with long-chain hydrocarbon and polyoxyalkylene groups, which can be used as emulsifiers and solubilizers and for thickening aqueous, anionic surfactant-containing preparations.

A particular object of the invention is to provide polyacrylate esters with long-chain hydrocarbon and polyoxyalkylene groups which have significantly better physiological properties compared to products currently available.

Another object of the invention is to provide polyacrylate esters with long-chain hydrocarbon and polyoxyalkylene groups which have as narrow a molecular weight distribution as possible and are as free as possible from monomeric and/or low molecular weight portions.

These and other objects are achieved by the invention disclosed below.

It has been discovered that the desired properties are provided by those polyacrylate esters which are obtained by the transesterification of alkyl polyacrylate ester with a polyoxyalkylene monool, wherein the alkyl polyacrylate ester, up to 50% of which may be replaced by the corresponding methacrylate esters, is obtained by free radical polymerization and the alkyl groups of which contain 1 to 8 carbon atoms and wherein the polyoxyalkylene monool is of the average formula

wherein
$R^1$ is an alkyl group with 8 to 30 carbon atoms, an alkenyl group with 8 to 22 carbon atoms or a monoalkyl- or dialkylphenyl group with 6 to 16 carbon atoms per alkyl group, wherein up to 40% of the Ri groups may be replaced by alkyl groups with 1 to 4 carbon atoms,
n has a value of 2, 3 or 4 and an average value of 2.0 to 2.5 in the average molecule and
x has a value of 10 to 200, in such amount, that 5 to 70% of the ester groups are transesterified in the presence of a transesterification catalyst at a temperature from 70° to 170° C. arid optionally in the presence of a solvent.

DESCRIPTION OF THE INVENTION

Starting compounds for preparing the long-chain alkoylated hydrocarbonyl group containing polyacrylate esters of the invention are alkyl polyacrylate esters which are synthesized by free radical polymerization, wherein the alkyl groups of the alkyl polyacrylate esters have 1 to 8 carbon atoms and are preferably linear. Particularly preferred are alkyl polyacrylate esters having alkyl groups with 1 to 4 carbon atoms, such as the methyl, ethyl, propyl and butyl group. In particular, the methyl and ethyl groups are preferred, since the ethanol or methanol, which is set free in the course of the transesterification, is more easily removed from the reaction mixture, for example, by distillation. It is therefore of decisive importance that the polyacrylate esters obtained by free radical polymerization are essentially free of low molecular weight portions and have a molecular weight distribution which corresponds to the Poisson distribution at least approximately. This distribution is retained during the transesterification so that, in contrast to the products obtained by copolymerization of a monomer mixture, the inventive products are also essentially free of low molecular weight products or oligomeric portions.

The inventive compounds with the desired characteristics are obtained due to transesterification of these alkyl polyacrylate esters with polyoxyalkylene monools of the average formula

wherein the groups and subscripts have the meanings set forth below.

The $R^1$ groups can be the same or different and represent an alkyl group, an alkenyl group or a monoalkyl- or dialkylphenyl group.

The alkyl group has 8 to 30 carbon atoms. Examples of such alkyl groups are the octyl, decyl, undecyl, dodecyl, stearyl or behenyl group. Preferred are alkyl groups with 14 to 22 carbon atoms and particularly those which are derived from fatty alcohols, which were obtained from natural fatty acids by reduction.

The alkenyl group has 8 to 22 carbon atoms and preferably 8 to 18 carbon atoms. Particularly preferred is the alkenyl group of an unsaturated fatty alcohol, such as the oleyl or linoleyl group.

The monoalkyl- or dialkylphenyl group has 6 to 16 carbon atoms in the alkyl group or groups. Preferred alkylphenyl groups are the mono- or dioctyl-, -nonyl-, -decyl- or -dodecylphenyl group.

It is also permissible to replace up to 40% of the $R^1$ groups by alkyl groups with 1 to 4 carbon atoms.

In formula I, n indicates the number of carbon atoms of the oxyalkylene groups and has a value of 2, 3 or 4 per oxyalkylene unit. It is therefore a question of oxyethylene, oxypropylene and oxybutylene units. In the average molecule, n has an average value of 2.0 to 2.5 and preferably of 2.0 to 2.3. A minimum hydrophilicity of the inventive compounds is ensured by these means.

Subscript x corresponds to the number of oxyalkylene units and has a value of 10 to 200 and preferably of 40 to 60. These values also are average values.

The polyoxyalkylene monools of formula I are reacted with alkyl polyacrylate esters in such quantitative ratios that 5 to 70%, preferably 20 to 70% and particularly 30 to 70%, of the ester groups are transesterified. The degree of transesterification can be followed from the amount of alkanol which originates from the alkyl polyacrylate ester.

The transesterification takes place in the presence of a transesterification catalyst. Such catalysts are known to those skilled in the art. Examples of these catalysts are i-propyl titanate or n-butyl titanate, potassium or sodium methylate, p-toluenesulfonic acid, methanesulfonic acid or trifluoroacetic acid.

It is usually advantageous to carry out the reaction in a solvent; toluene or xylene is the preferred solvent.

The transesterification temperature is about 70° to 170° C. and particularly about 90° to 150° C.

Water solubility, hydrophilicity, solubilizing capability and compatibility with anionic surfactants are affected by the choice of the $R^1$ groups and by the polymer subscripts x and n.

Quite generally, it may be noted that the water solubility increases as the ethylene oxide content increases and as the number of carbon atoms of the alkyl or alkenyl group decreases. In this connection, it is also advantageous to replace 40% of the $R^1$ groups by alkyl groups with 1 to 4 carbon atoms.

Up to 50 mole percent of alkyl acrylate esters can be replaced by the corresponding alkyl methacrylate esters.

It is clear to those skilled in the art that the alkyl polyacrylate esters which are used as starting compounds for the transesterification reaction may also contain other copolymerized comonomers, such as styrene, acrylamide, acrylonitrile or alkyl methacrylate esters.

Those polymers in which $R^1$ is an alkyl or alkenyl group with at least 14 carbon atoms or a monoalkyl- or dialkylphenyl group, the alkyl group of which has 6 to 16 carbon atoms, are particularly suitable when the compounds of the invention are to be used as solubilizers and emulsifiers or coemulsifiers.

When the inventive compounds are used as emulsifiers, it must be noted that the hydrophilicity of the emulsifier must be adapted to the oil phase that is to be emulsified (HLB principle). It is possible to adjust the hydrophilicity (HLB value) to the required value by appropriately selecting the polymer subscripts n and x. In general, those polymers are preferred in which n assumes a value between 2 and 2.5. In this case, subscript x usually assumes a value of 10 to 50.

With regard to the thickening action of the inventive compounds in the presence of anionic surfactants (shampoo formulations), those products are preferred in which $R^1$ is an alkyl or alkenyl group with 16 to 22 carbon atoms. The use of polyethylene oxide segments with 30 to 60 monomer units has proven to be advantageous here. The use of propylene oxide as a comonomer in the polyether segments, in addition to ethylene oxide, lowers compatibility with anionic surfactants. However, by introducing relatively small amounts of propylene oxide, the crystallization of the inventive compounds can be prevented and, with that, their handling is improved. Small amounts of butylene oxide can also be used for the same purpose. Compatibility with anionic surfactants can be improved even further, if ethoxylates of lower molecular weight aliphatic alcohols, such as methanol, are used for the transesterification in addition to the longer-chain ethoxylated fatty alcohols.

The following examples of the invention illustrate the best mode currently contemplated for carrying out the invention, and show the synthesis of compounds of the invention and their thickening effect. However, it is understood that these examples are given by way of illustration and must not be considered to limit the invention in any manner.

EXAMPLE 1

Synthesis of Polymethacrylate by Free Radical Polymerization (Not of the Invention)

A solution of 0.6 g of azodiisobutyronitrile and 20.2 g of dodecyl mercaptan in 50 g of toluene and 280 g (approximately 3.25 moles) of methyl acrylate is added within 2 hours to a reactor filled with 53 g of toluene; the solvent added has a temperature of 100° C. and is under an atmosphere of nitrogen. After that, a further 0.9 g of azodiisobutyronitrile, dissolved in 20 g of methyl ethyl ketone, are added within 0.5 hours. Finally, the reaction mixture is heated for a further hour at the same temperature of 100° C. At the end of the reaction, the solvent is distilled off. A colorless, viscous liquid, with a refractive index of 1.4902, remains behind. Gel chromatographic analysis reveals that the polymer obtained has a number average molecular weight of $\overline{M}_n$ of 1950 and a weight average molecular weight $\overline{M}_w$ of 3330; the nonuniformity coefficient accordingly is 1.71. The residual monomer content amounts to less than 0.1%.

EXAMPLES 2 to 4

Synthesis of Poly(Methyl Acrylates) of Different Molecular Weights by Free Radical Polymerization (Not of the Invention)

The method of Example 1 is followed with the exception that the content of dodecyl mercaptan is lowered. The dependence of the number average and weight average molecular weights on the content of dodecyl mercaptan is shown. The residual monomer content is less than 0.1% in both cases.

TABLE 1

| Poly(methyl acrylate) from Example | Dodecyl Mercaptan (% by weight) | Molecular Weight $M_n$ | Molecular Weight $M_w$ | Non-uniformity coefficient |
|---|---|---|---|---|
| 2 | 13.5 | 836 | 1,302 | 1.56 |
| 3 | 2.95 | 4,453 | 11,346 | 2.55 |

TABLE 1-continued

| Poly(methyl acrylate) from Example | Dodecyl Mercaptan (% by weight) | Molecular Weight $M_n$ | Molecular Weight $M_w$ | Non-uniformity coefficient |
|---|---|---|---|---|
| 4 | 0.43 | 16,750 | 68,500 | 4.09 |

EXAMPLE 5

Synthesis of Poly(n-Butyl Acrylate) by Free Radical Polymerization (Not of the Invention)

The method of Example 1 is followed with the difference that n-butyl acrylate is used instead of methyl acrylate.

Gel chromatographic analysis reveals that the polymer obtained has a number average molecular weight $\overline{M}_n$ of 1900 and a weight average molecular weight $\overline{M}_w$ of 3300; the nonuniformity coefficient accordingly is 1.73. The residual monomer content is determined to be less than 0.1%.

EXAMPLE 6

Synthesis of Poly(2-Ethylhexyl Acrylate) by Free Radical Polymerization (Not of the Invention)

The procedure or Example 1 is followed with the difference that 2-ethylhexyl acrylate is used instead of methyl acrylate.

Gel chromatographic analysis reveals that the polymer obtained has a number average molecular weight $\overline{M}_n$ of 1,800 and a weight average molecular weight $\overline{M}_w$ of 3,030; the nonuniformity coefficient accordingly is 1.68. The residual monomer content is determined to be about 0.1%.

EXAMPLE 7

Synthesis of a Methyl Acrylate/Methyl Methacrylate Copolymer by Free Radical Polymerization (Not of the Invention)

The method of Example 1 is followed, with the exception that, instead of an amount of 280 g (approximately 3.25 moles) of methyl acrylate, 140 g (approximately 1.61 moles) of methyl acrylate and 140 g (approximately 1.4 moles) of methyl methacrylate are used. Gel chromatographic analysis reveals that the polymer obtained has a number average molecular weight $\overline{M}_n$ of 2,280 and a weight average molecular weight $\overline{M}_w$ of 4,390; the nonuniformity coefficient accordingly is 1.93. The residual monomer content is determined to be about 0.15%.

EXAMPLE 8

Synthesis of Oleyloxy Polyethylene Oxide Monool (Not of the Invention)

Oleyl alcohol (268 g, approximately 1 mole) and 7.0 g (approximately 0.1 moles) of potassium methylate are added to a reactor, which is then flushed carefully with pure nitrogen and heated to 110° C. After that, 2,420 g (approximately 55 moles) of ethylene oxide are added at such a rate, that within the reactor the temperature does not exceed 120° C. and the pressure does not exceed 6 bar. After all of the ethylene oxide has been passed into the reactor, the temperature is maintained at 115° C., until a constant pressure indicates the end of the reaction. Subsequently, 95.7 g (approximately 1.65 moles) of propylene oxide are added and the temperature once again is held at 115° until the pressure stays constant. Finally, the unreacted monomers are removed under vacuum at 80° to 90° C.

The product obtained is neutralized with the help of dilute phosphoric acid, the water is removed by distillation and the potassium phosphate formed is removed by filtration. From determination of the hydroxyl number and assuming a functionality of 1, the molecular weight is found to be 2310.

EXAMPLES 9 TO 25

Synthesis of Various Alkyloxy and Alkylaryloxy Polyalkylene Oxide Monools (Not of the Invention)

The synthesis and working up of various alkoxylates of alkanols and alkylphenols is carried out basically as described in Example 8 by the addition reaction of alkylene oxides in the presence of alkaline catalysts and subsequent neutralization with dilute phosphoric acid.

Examples of the starting alcohols used, of the alkylene oxides according to their nature and the number of moles, as well as of the molecular weights, which were ascertained by determining the OH number, are given in Table 2.

TABLE 2

| Polyalkylene Oxide Example No. | Starter | EO [moles] | PO [moles] | BO [moles] | MW [OH No.] |
|---|---|---|---|---|---|
| 8 | OLA | 50 | 1.5* | — | 2,310 |
| 9 | OLA | 10 | — | — | 646 |
| 10 | OLA | 25 | 19.0 | — | 2,040 |
| 11 | OLA | 40 | 8.5 | — | 2,280 |
| 12 | OLA | 44 | — | 3.7 | 2,149 |
| 13 | TFA | 2 | — | — | 352 |
| 14 | TFA | 20 | — | — | 1,152 |
| 15 | TFA | 50 | 1.5* | — | 2,040 |
| 16 | BHA | 50 | 1.5* | — | 2,290 |
| 17 | C21 | 50 | 1.5* | — | 2,377 |
| 18 | CTA | 50 | 1.5* | — | 2,440 |
| 19 | DDO | 50 | 1.5* | — | 2,226 |
| 20 | OCA | 20 | 1.5* | — | 967 |
| 21 | MEA | 21 | 1.5* | — | 949 |
| 22 | MEA | 43 | 1.5* | — | 1,970 |
| 23 | NP | 10 | — | — | 660 |
| 24 | NP | 50 | — | — | 2,550 |
| 25 | DNP | 49 | — | — | 1,982 |

*Propylene oxide at the hydroxy-functional end of the chain

Legend:
MEA = methanol
OCA = 1-octanol
DDO = 1-dodecanol
CTA = cetyl alcohol
OLA = oleyl alcohol
TFA = tallow fatty alcohol
C21 = Exxal 21 ®
BHA = behenyl alcohol
NP = nonylphenyl
DNP = dinonylphenol

EXAMPLE 26

Synthesis of a Transesterification Product from Poly(Methyl Acrylate) and Alkoxylated Oleyl Alcohol The poly(methyl acrylate) (92.3 g) of example 1, dissolved in 554 g of toluene, is heated together with 462 g (approximately 0.2 moles) of an oleyloxy polyether of Example 8 under nitrogen. To begin with, traces of water possibly present are removed by azeotropic distillation. After that, 2 g of isopropyl titanate is added. The methanol, formed by the transesterification, is removed by fractional distillation from the toluene. After 2 hours and after 4 hours of reaction time, 2 g of isopropyl titanate are added. The reaction is finished after about 6 hours. A stillhead temperature of about 110° C. indicates the end of the reaction.

According to gel chromatographic analysis, 125 g of oleyloxy polyether are unreacted; this corresponds to a conversion of 72.9%. The methanol content in the distillate is 4.36 g, corresponding to a conversion of 68.1% of that theoretically possible. It follows from this that about 70.5% of the ester groups of the poly(methyl acrylate) have been converted. After removal of the transesterification catalyst by hydrolysis and filtration, the Gardner color number of the product is 2 to 3.

EXAMPLES 27 TO 49

Transesterification of Various Polyacrylates with Different Fatty Alcohol Alkoxylates The procedure of Example 26 is followed, with the exception that polyacrylates of different molecular weights and with a different number of carbon atoms, as well as, in one case, a methyl acrylate/methyl methacrylate copolymer are used as ester group-containing components (see Examples 1 to 7). Moreover, different fatty alcohol alkoxylates are used, which differ with respect to the number of carbon atoms of the alkyl, alkylacryl and alkenylphenyl groups, the molecular weight of the polyether segment and the composition of the latter (see Examples 8 to 25). The theoretical degree of substitution refers to the ratio of the number of substituted ester groups to the number of ester groups originally present. In practice, the degree of substitution is obtained from gel chromatographic analysis or from the amount of low molecular weight alcohol that has been isolated. The nature and amount of the components, as well as the theoretical and the practical degree of substitution are given in Table 3. When poly(2-ethylhexyl acrylate) is used, the transesterification is carried out without the use of a solvent under reduced pressure.

EXAMPLES 50 TO 53

Synthesis of Transesterification Products Using Two Different Polyalkylene Oxide Monools (Cotransesterification)

The procedure of Example 26 is followed with the exception that two different polyether monools are used simultaneously (cotransesterification). The nature and amount of the polyoxyalkylene oxide monool, as well as the theoretical and practical degrees of substitution are given in Table 3.

TABLE 3

| Example No. | Polyacrylate Example No. | Polyacrylate Amount [g] | Polyalkylene Oxide Example No. | Polyalkylene Oxide Amount [g] | Degree of Substitution theor. [mole %] | Degree of Substitution pract. [mole %] |
|---|---|---|---|---|---|---|
| 27 | 1 | 92.3 | 9 | 129.2 | 20 | 19.0 |
| 28 | 1 | 92.3 | 10 | 408.0 | 20 | 6.4 |
| 29 | 1 | 92.3 | 11 | 456.0 | 20 | 13.2 |
| 30 | 1 | 92.3 | 12 | 429.8 | 20 | 12.6 |
| 31 | 1 | 92.3 | 8 | 693.0 | 30 | 21.1 |
| 32 | 1 | 92.3 | 8 | 924.0 | 40 | 26.5 |
| 33 | 1 | 92.3 | 8 | 1155.0 | 50 | 34.0 |
| 34 | 3 | 88.7 | 8 | 462.0 | 20 | 13.4 |
| 35 | 2 | 99.5 | 8 | 462.0 | 20 | 16.8 |
| 36 | 4 | 86.7 | 8 | 462.0 | 20 | 13.3 |
| 37 | 1 | 92.3 | 13 | 70.4 | 20 | 19.0 |
| 38 | 1 | 92.3 | 14 | 230.4 | 20 | 18.0 |
| 39 | 1 | 92.3 | 15 | 408.0 | 20 | 15.7 |
| 40 | 1 | 92.3 | 20 | 193.4 | 20 | 17.5 |
| 41 | 1 | 92.3 | 19 | 445.2 | 20 | 15.5 |
| 42 | 1 | 92.3 | 18 | 488.0 | 20 | 14.2 |
| 43 | 1 | 92.3 | 17 | 475.4 | 20 | 14.6 |
| 44 | 1 | 92.3 | 16 | 458.0 | 20 | 14.5 |
| 45 | 1 | 92.3 | 23 | 132.0 | 20 | 17.6 |
| 46 | 1 | 92.3 | 24 | 510.0 | 20 | 13.9 |
| 47 | 1 | 92.3 | 25 | 396.4 | 20 | 15.7 |
| 48 | 7 | 184.6 | 8 | 346.5 | 15 | 11.2 |
| 49 | 5 | 137.5 | 8 | 462.0 | 20 | 13.8 |
| 50 | 1 | 92.3 | 8/21 | 367/29 | 20 | 15.1 |
| 51 | 1 | 92.3 | 8/21 | 302/57 | 20 | 15.0 |
| 52* | 1 | 92.3 | 8/22 | 367/59 | 20 | 14.8 |
| 53 | 1 | 92.3 | 8/22 | 302/118 | 20 | 15.3 |
| 54 | 6 | 197.3 | 24 | 306 | 12 | 6.5 |
| 55* | 1 | 92.3 | 22 | 394 | 20 | 15.2 |

* = Comparison Example

APPLICATION EXAMPLES

To demonstrate their thickening effect, the inventive polyacrylate esters with long-chain alkoxylated hydrocarbonoxy groups are used as 40% solutions in 1,2-propylene glycol/water (=2/1) in the shampoo formulations below:

Phase A:
Inventive thickening agent (40%): x%
Sodium lauryl ether sulfate (28%): 43%
Perfume oil (Levona, Dfillberg): 0.5%

Phase B:
Tego betaine L7*: 10%
Water: to 100% *Tego Betaine L7=cocamidopropyl-betaine (1-alkoylamino-3-dimethyl-ammonium-propane-3-carboxymethyl-betaine)

To begin with, phases A and B were prepared separately at room temperature. Subsequently, phase A is added to phase B with vigorous stirring.

The viscosities obtained are summarized in Table 4 below.

TABLE 4

| Inventive Thickener of Example | Concentration [%] | Viscosity (25° C., Brookfield LVF) [mPa × s] |
|---|---|---|
| 26 | 1.0 | 4,800 |
|  | 2.0 | 9,600 |
|  | 3.0 | 19,000 |
| 31 | 1.0 | 1,880 |
|  | 2.0 | 9,500 |
| 33 | 1.0 | 2,900 |
|  | 2.0 | 14,000 |
| 34 | 2.0 | 8,900 |
|  | 3.0 | 21,000 |
| 39 | 1.0 | 2,000 |
|  | 2.0 | 9,500 |
|  | 3.0 | 19,000 |
| 42 | 1.0 | 1,700 |
|  | 2.0 | 8,500 |
|  | 3.0 | 17,500 |
| 44 | 1.0 | 2,000 |
|  | 2.0 | 9,500 |
|  | 3.0 | 20,500 |
| 55* | 3.0 | 8,000 |

*Comparison

We claim:

1. Polyacrylate ester with long-chain alkoxylated hydrocarbonoxy groups obtained by transesterification of an alkyl polyacrylate ester with a polyoxyalkylene monool, wherein the alkyl polyacrylate ester, up to 50% of which may be replaced by the corresponding methacrylate, is obtained by free radical polymerization and the alkyl groups of which contain 1 to 8 carbon atoms and wherein the polyoxyalkylene monool is of the average formula $$R^1O-(C_nH_{2n}O-)_xH$$

wherein
- $R^1$ can be the same or different in the monool and is an alkyl group with 9 to 30 carbon atoms, an alkenyl group with 8 to 22 carbon atoms or a monoalkyl- or dialkylphenyl group with 6 to 16 carbon atoms per alkyl group, and up to 40% of the $R^1$ groups may be replaced by alkyl groups with 1 to 4 carbon atoms,
- n has a value of 2, 3 or 4 and an average value of 2.0 to 2.5 in an average molecule and
- x has an average value of 10 to 200, in such amounts, that 5 to 70% of the ester groups are transesterified, in the presence of a transesterification catalyst at a temperature of from 70° to 170° C. and, optionally, in the presence of a solvent.

2. The polyacrylate ester of claim 1 obtained by the transesterification of an alkyl polyacrylate ester with a polyoxyalkylene monool in such amount that 20 to 70% of the ester groups are transesterified.

3. The polyacrylate ester of claim 1, obtained by the transesterification of an alkyl polyacrylate ester with a polyoxyalkylene monool in such amount that 30 to 70% of the ester groups are transesterified.

4. The polyacrylate ester of claim 1 in which $R^1$ is an alkyl group with 14 to 22 carbon atoms.

5. The polyacrylate ester of claim 1, in which $R^1$ is an alkenyl group with 8 to 18 carbon atoms.

6. The polyacrylate ester of claim 1 in which $R^1$ is a monoalkylphenyl group, the alkyl group of which has 6 to 12 carbon atoms.

7. The polyacrylate ester of claim 1, in which the transesterification is carried out with a polyoxyalkylene monool the subscript n of which has an average value of 2.0 to 2.3.

8. The polyacrylate ester of claim 1, in which the transesterification is carried out with a polyoxyalkylene monool, the subscript x of which has an average value of 40 to 60.

9. An emulsifier for an aqueous preparation containing an anionic surfactant comprising the polyacrylate ester defined in claim 1.

10. The emulsifier defined in claim 9, wherein the aqueous preparation is a cosmetic.

11. A solubilizer for an aqueous preparation containing an anionic surfactant comprising the polyacrylate ester defined in claim 1.

12. The solubilizer defined in claim 11, wherein the aqueous preparation is a cosmetic.

13. A thickener for an aqueous preparation containing an anionic surfactant comprising the polyacrylate ester defined in claim 1.

14. The thickener defined in claim 13, wherein the aqueous preparation is a cosmetic.

* * * * *